United States Patent
Matthews et al.

(10) Patent No.: US 6,740,635 B2
(45) Date of Patent: May 25, 2004

(54) ANTIVIRAL LINEAR POLYMERS

(75) Inventors: Barry Ross Matthews, Olinda (AU); George Holan, Brighton (AU)

(73) Assignee: Biomolecular Research Institute Ltd., Parkville (AU)

(*) Notice: Subject to any disclaimer, the term of this patent is extended or adjusted under 35 U.S.C. 154(b) by 65 days.

(21) Appl. No.: 09/929,014

(22) Filed: Aug. 15, 2001

(65) Prior Publication Data

US 2002/0025919 A1 Feb. 28, 2002

Related U.S. Application Data

(63) Continuation of application No. 09/230,189, filed as application No. PCT/AU97/00446 on Jul. 17, 1997, now abandoned.

(30) Foreign Application Priority Data

Jul. 17, 1996 (AU) .............................................. PO 1043

(51) Int. Cl.$^7$ ...................... A61K 31/795; A61K 38/02; C07K 2/00; C08G 69/36
(52) U.S. Cl. ........................... 514/8; 525/54.2; 530/322
(58) Field of Search .............................. 514/2, 7, 8, 12, 514/562; 530/300, 322, 345, 350, 352, 395, 402, 408; 525/54.1, 54.2, 535; 562/101, 102, 103

(56) References Cited

U.S. PATENT DOCUMENTS

| | | | |
|---|---|---|---|
| 5,869,457 A | 2/1999 | Jansen et al. | 514/21 |
| 6,007,803 A | 12/1999 | Mandeville, III et al. | 424/78.1 |
| 6,034,129 A | 3/2000 | Mandeville, III et al. | 514/549 |
| 6,060,235 A | 5/2000 | Neenan et al. | 435/5 |

FOREIGN PATENT DOCUMENTS

| | | |
|---|---|---|
| EP | 254419 | 1/1988 |
| WO | 95-340595 | 12/1995 |
| WO | 96/15810 | 5/1996 |

OTHER PUBLICATIONS

Roy et al.; "Michael Addition of Poly-$_L$-lysine to N-Acryloylated Sialosides, Syntheses of Influenza Virus Haemagglutinin Inhibitor and Group B Meningococcal Polysaccharide Vaccines"; J. Chem. Soc.; 1993; pp. 264–265.
Mammen et al.; "Effective Inhibitors and Hemagglutination by Influenza Virus Synthesized from Polymers Having Active Ester Groups. Insight into Mechanism of Inhibition"; Journal of Medicinal Chemistry; vol. 38, No. 21; 1995; pp. 4179–4190.
Sigal et al.; "Polyacrylamides Bearing Pendant α-Sialoside Groups Strongly Inhibit Agglutination of Erythrocytes by influenza Virus: The Strong Inhibition Reflects Enhanced Binding Through Cooperative Polyvalent Interactions"; Journal of American Chemistry Society; vol. 118, No, 16; Apr. 24, 1996; pp. 3789–3800.
Itoh et al.; "Suppression of Influenza Virus infection by an N–Thioacetylneuraminic Acid Acrylamide Copolymer Resistant To Neuraminidase"; Virology; vol. 212; 1995; pp. 340–347.
Matrosovich et al.; Synthetic Polymeric Sialoside Inhibitors of Influenza Virus Receptor–binding Activity; FEBS Letters; vol. 272, No. 1,2; Oct. 1990; pp. 209–212.
Mochalova et al.; "Synthetic Polymeric Inhibitors of Influenza Virus Receptor–Binding Activity Suppress Virus Replication"; Antiviral Research; vol. 23; 1994; pp. 179–190.
Sparks et al.; "Neuraminidase–Resistant Hemagglutination Inhibitors: Acrylamide Copolymers Containing A C–Glycoside of N–Acetylneuraminic Acid"; Journal of Medicinal Chemistry; vol. 36, No. 6; 1995; pp. 778–783.
Spaltenstein et al.; "Polyacrylamides Bearing Pendant α–Sialoside Groups Strongly Inhibit Agglutination of Erythrocytes by Influenza Virus"; J. Am. Chem. Soc.; vol. 113; 1991; pp. 686–687.
Lees et al.; "Polyacrylamides Bearing Pendant α–Sialoside Groups Strongly Inhibit Agglutination of Erythrocytes by Influenza A Virus: Multivalency and Steric Stabilization of Particulate Biological Systems"; Journal of Medicinal Chemistry; vol. 37, No. 20; 1994; pp. 3417–3433.
Nagy et al.; "Carbohydrate Materials Bearing Neuraminidase–Resistant C–Glycosides of Inventivity of Influenza Virus"; Journal of Medicinal Chemistry; vol. 35, No. 23; 1992; pp. 4501–4502.
Roy et al.; "Synthesis of Esterase–Resistant 9–o–Acetylated Polysialoside as Inhibitor of Influenza C Virus Hemagglutinin"; Chem. Int. Ed. Engl.; vol. 31, No. 11; 1992; pp. 1478–1481.
Gamian et al.; "Inhibition of Influenza A Virus Hemagglutinin and Induction of Interferon by Synthetic Sialylated Glycoconjugates"; J. Microbiol.; vol. 37; 1991; pp. 233–237.
Yang, et al., "Inhibitory effect of polyionic compounds on the adsorption of herpes simplex virus type 1 (KOS)", *Antiviral Chemistry & Chemotherapy*, 8:1 32–37 (1997).
Sinibaldi, et al., "Effect of Biological and Synthetic Polymers on BK Virus Infectivity and Haemagglutionation", *J. of Chemotherapy*, 4:1 16–22 (1992).
Roy, et al., "Solid Phase Synthesis of Denditic Dialoside Inhibitors of Influenza A Virus Haemagglutinin", *J.C.S., Chem. Commun.*, 1869–1972 (1993).
Bagasra, et al., "Anti–Human Immunodeficiency Virus Type 1 Activity of Sulfated Monosaccharides. Comparison with sulfated Polysaccharides and Other Polyions", *J. Infectious Diseases*, 164: 1082–90 (1991).
Hosoya, et al., "Inhibitory effects of polycations on the replication of enveloped viruses (HIV, HSV, CMV, RSV, influenze A virus and togaviruses ) *in vitro"*, *Antiviral Chem. & Chemo.*, 2:4 243–248 (1991).
Mathur, et al., "Antiviral Activity of Some New Cationic Polyamino Acids", *Indian J. of Experimental Biology*, 20: 227–229 (1982).

*Primary Examiner*—Jeffrey E. Russel
(74) *Attorney, Agent, or Firm*—Foley & Lardner, LLP

(57) ABSTRACT

An antiviral compound comprises a linear non-carbohydrate polymer having a plurality of side chain groups, wherein at least one of the side chain groups has an anionic- or cationic-containing moiety bonded or linked thereto.

18 Claims, No Drawings

ANTIVIRAL LINEAR POLYMERS

This application is a continuation of application Ser. No. 09/230,189, filed Mar. 18, 1999, now abandoned, which is the National Stage of International Application No. PCT/AU97/00446, filed Jul. 17, 1997.

FIELD OF THE INVENTION

This invention relates to antiviral agents, and in particular it relates to polyionic, especially polyanionic linear polymers which have been found to have significant antiviral activity, particularly against human immunodeficiency virus (HIV), respiratory syncytial virus (RSV), human influenza virus A and B, Hepatitis B virus (HBV) and other enveloped viruses.

BACKGROUND OF THE INVENTION

It has been established that certain sulfonated polysaccharide compounds have antiviral activity when screened against HIV, however these compounds are relatively unstable and accordingly large amounts of these compounds are required to obtain effective antiviral effects. In addition, many of these compounds, including heparin and dextran sulfate for example, are potent anticoagulants and because of this activity they are not particularly suited for clinical use as antiviral agents.

International Patent Application No. PCT/AU95/00350 (WO 95/34595) discloses a class of antiviral compounds comprising a dendrimer such as a polyarnidoamine or polylysine dendrimer having a plurality of terminal groups, wherein at least one of the terminal groups has an anionic- or cationic-containing moiety bonded or linked thereto, particularly a sulfonic acid-containing, a carboxylic acid-containing or a trimethylammonium-containing moiety.

The present invention provides a new class of antiviral agents based on a particular type of polyionic polymer having a linear "backbone", which have substantial antiviral activity against HIV1 and HIV2, RSV, HBV and human influenza virus A and B. These compounds are well suited for prophylactic and therapeutic use as antiviral agents in humans.

SUMMARY OF THE INVENTION

According to the present invention, there is provided an antiviral compound comprising a linear noncarbohydrate polymer having a plurality of side chain groups wherein at least one of said side chain groups has an anionic-or cationic-containing moiety bonded or linked thereto.

Particularly preferred antiviral compounds of the present invention are linear polymers having sulfonic acid-containing moieties, carboxylic acid-containing moieties, phosphoric or phosphonic acid-containing moieties, boronic acid-containing moieties, neuraminic or sialic acid-containing moieties or moieties containing neuraminic or sialic acid modified in the 4- or other position thereof, linked to side chain groups thereof.

The compounds of the invention are referred to herein as polyionic polymers, and this term is used throughout this specification to include not only the polymers per se, but also their pharmaceutically or veterinarily acceptable salts, for example the alkaline metal or alkaline earth metal salts such as the sodium, potassium or calcium salts.

DETAILED DESCRIPTION OF THE INVENTION

Preferred polyionic polymers in accordance with the present invention are linear polymers having the general formula I:

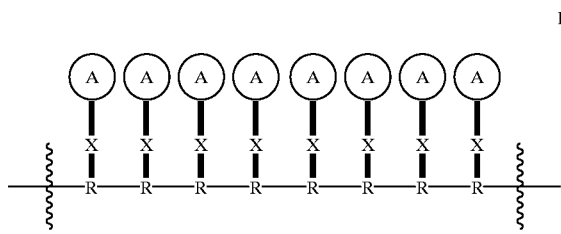

wherein:

R is a non-carbohydrate monomer unit forming a linear polymer backbone;

X is an optional linking group on the side chain groups of monomer units R; and

A is an anionic-containing moiety.

Thus, in accordance with the present invention, the preferred linear polymers are polyanionic materials formed by the conjugation of anionic moieties (A) to a linear non-carbohydrate polymer backbone (made up of a plurality of monomer units R), optionally through linking groups (X). The resultant polyanionic linear polymers have a molecular weight range distribution of repeating units to give a desired median range of molecular weight distribution. Desirably, the median range of molecular weight distribution is from 1,000 to 1,000,000, preferably from 10,000 to 600,000.

The monomer unit R is preferably amine or amide moiety, more preferably an amino acid moiety. A particularly preferred monomer unit is a lysine moiety. Poly-L-lysines having various molecular weight ranges are available commercially from Sigma Chemical Company.

The anionic moiety A can be linked to reactive side chain groups on the linear polymer backbone either directly or via a variety of functional linking groups X such as, but not limited to, esters, amides, ethers, thioethers, amines, ureas, thioureas, carbamates and carbonates.

The optional linking group X may also act as a spacer between the polymer and the anionic moiety A, and may consist of an alkyl chain (optionally substituted or branched), an alkoxy, polyalkoxy, alkylthio or polyalcylthio chain (optionally substituted), or an alkenyl, multiple alkenyl, alkynyl or multiple alkynyl chain (optionally substituted). Suitable spacer chains include groups of the formula —(CH$_2$)$_n$—Z—(CH$_2$)$_n$—, wherein Z is —CH$_2$—, —CH=CH—, —C≡C—, —O— or —S—, and n is an integer of from 1 to 15.

In accordance with the present invention, at least one, and preferably a substantial number, of the reactive side chain groups on the backbone of the linear polymer has an anionic- or cationic-containing moiety covalently bonded thereto. The side chains of the polymer backbone may terminate in amino groups or other functional reactive groups such as OH, SH, or the like, which subsequently can be reacted with the anionic or cationic moieties. Where the side chain groups of the polymer backbone are amine groups, the anionic- or cationic-containing moiety may be linked to the polymer backbone by a variety of functional groups including amide and thiourea linkages. Preferred anionic- or cationic-containing moieties which may be bonded or linked to the side chain groups of the polymer backbone include sulfonic acid-containing moieties, carboxylic acid-containing moieties (including neuraminic and sialic acid-containing moieties and modified neuraminic and sialic acid-containing moieties), boronic acid-containing moieties, phosphoric and phosphonic acid-containing moieties (including esterified phosphoric and phosphonic acid-containing moieties) and trimethylamnonium-containing moieties.

Suitable anionic-and cationic-containing moieties which may be bonded or linked to the amino or other side chain groups of the linear polymers include, by way of example, the following groups (in which n is zero or a positive integer, more particularly n is zero or an integer of from 1 to 20):

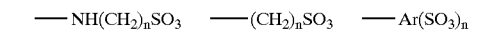
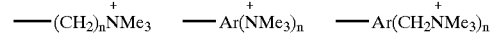
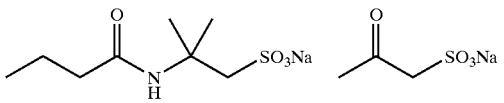
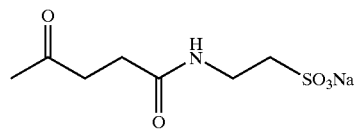
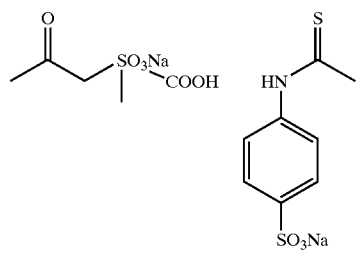
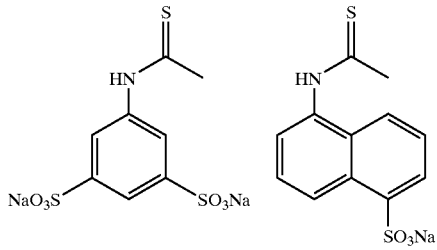
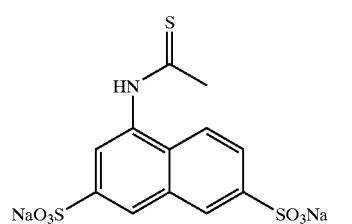

-continued

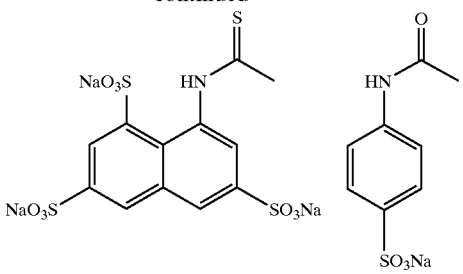
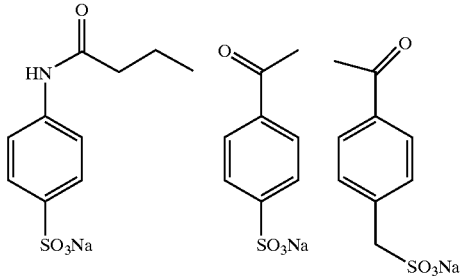
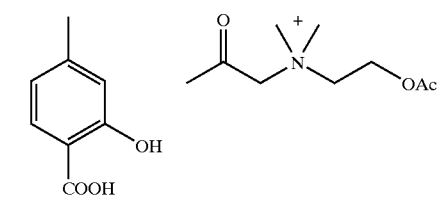
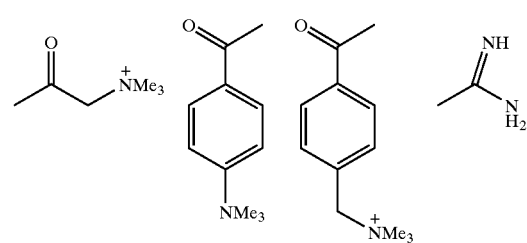
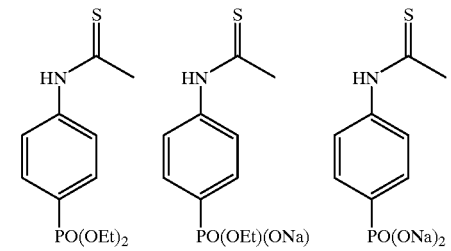
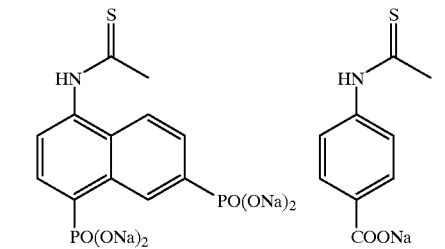

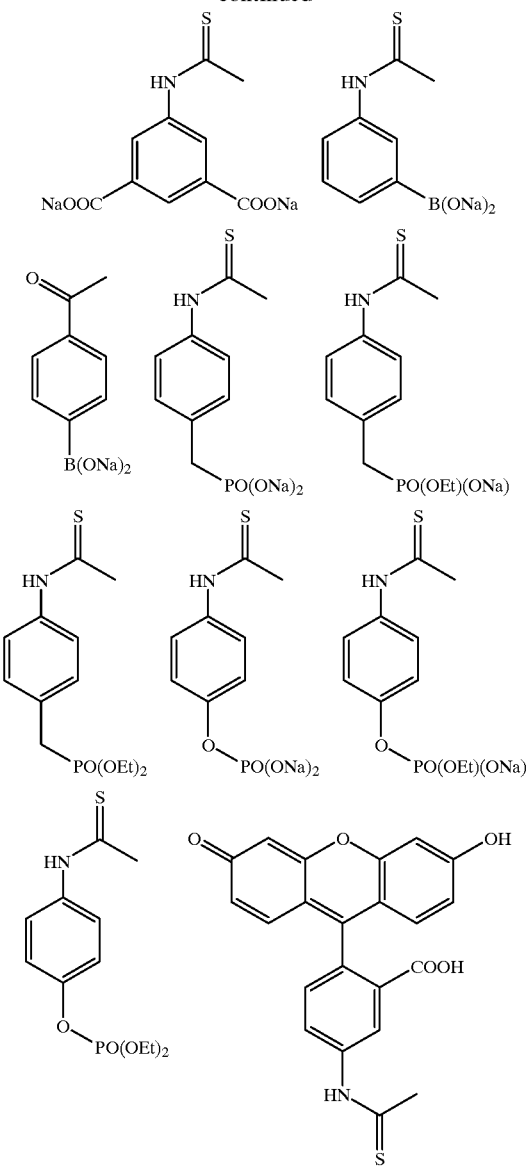

In addition to the above, various neuramiric or sialic acid-containing moieties or modified neuraminic or sialic acid-containing moieties may be bonded or linked to the side chain groups in accordance with this invention. These moieties include the various N- and O-substituted derivatives of neuraminic acid, particularly N- and O-acyl derivatives such as N-acetyl, O-acetyl and N-glycolyl derivatives, as well as moieties in which the neuraminic acid group is modified, particularly by substitution in the 4-position, with an amino, amido, cyano, azido or guanidino group.

The polyionic polymers of this invention may be prepared by standard chemical methods which are well known to persons skilled in this art. Suitable methods are described by way of example in the Examples below.

As previously described, the polyionic polymers of the present invention have been found to exhibit significant antiviral activity, particularly against enveloped viruses. Accordingly, these polyionic polymers are useful in prophylactic and therapeutic treatment of viral infections, for example infections by HIV1 and HIV2 and other enveloped viruses including DNA viruses such as Hepatitis B and RNA viruses including flaviviruses such as Hepatitis C, Bovine Viral Diarrhoea Virus and Japanese Encephalitis Virus (JEV). The polyionic polymers of the present invention may also be used in prophylactic or therapeutic treatment against Human Influenza Virus A and B, Rhinoviruses, Corona Viruses, Human Parainfluenza Virus, Respiratory Syncytial Virus (RSV), Varicella Zoster Virus (VZV), Human Cytomegalovirus (CMV), Epstein Barr Virus (EBV), Human Papilloma Virus (HPV), Adenoviruses, Herpes Simplex Virus (HSV) type 1 and 2, Measles Virus and Vesicular Stomatitis Virus (VSV).

Thus, in another aspect the present invention provides a pharmaceutical or veterinary composition for prophylactic or therapeutic antiviral treatment of a human or non-human animal, which comprises a polyionic polymer as broadly described above, in association with at least one pharmaceutically or veterinarily acceptable carrier or diluent.

The formulation of such compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences,* 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In another aspect, the present invention provides a method for prophylactic or therapeutic treatment of a viral infection in a human or non-human animal, which comprises administering to said human or animal a prophylactic- or therapeutic-antiviral-effective amount of a polyionic polymer as broadly described above.

In yet another aspect, this invention provides the use of a prophylactic- or therapeutic-antiviral-effective amount of a polyionic polymer as broadly described above in the prophylactic or therapeutic treatment of, or in the manufacture of a medicament for prophylactic or therapeutic treatment of a viral infection in a human or non-human animal.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, inhalation, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

The compositions may conveniently be presented in unit dosage form and may be prepared by any of the methods well known in the art of pharmacy. Such methods include the step of bringing the active component into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active component, in liposomes or as a suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables.

The active compound may also be formulated for delivery in a system designed to administer the active component intranasally or by inhalation, for example as a finely dispersed aerosol spray containing the active component.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system can be used, some of which are adapted for implantation.

The active component is administered in prophylactically or therapeutically effective amounts. A prophylactically or therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily oral doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

The active component according to the invention may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced into the udder via the teat;

(c) topical application, e.g. as a cream, ointment or spray applied to the skin; or (d) intravaginally, e.g. as a pessary, cream or foam.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Further features of the present invention will be apparent from the following Examples which are included by way of illustration, not limitation of the invention.

EXAMPLE 1

Preparation of Sodium 4-Sulfophenylthiourea Terminated Polylysines

A Solid sodium 4-sulfophenylisothiocyanate monohydrate (2.55g; 10 mmol) was added to a solution of poly-L-lysine (15–30 K) (Sigma Chemical Company) (1.0 g) in a mixture of water (20 ml) and N,N-dimethyl-N-allylamine buffer (pH 9.5; 15 ml). The resulting mixture was heated under nitrogen at 53° C. for 3 hours, when a ninhydrin test was negative. The cooled mixture was filtered and the filtrate concentrated to give a grey solid residue. The solid residue was redissolved in water and passed through a column of Amberlite IR 120(Na) and then concentrated. The crude product was purified by gel filtration (Sephadex LH20; water) and freeze dried to give sodium 4-sulfophenylthiourea terminated poly-L-lysine BRI2995 as a white fluffy solid (1.25 g).

B Similarly prepared were sodium 4-sulfophenylthiourea terminated polylysines of molecular weight fraction 1–4 K BRI2994, 4–15 K BRI2967. 150–300 K BRI2996.

EXAMPLE 2
Preparation of Sodium 3,6-Disulfonapthylthiourea Terminated Polylysines Solid sodium 3,6-Disulfonapthylisothiocyanate (200 mg; 0.51 mmol) was added to a solution of poly-L-lysine (15–30 K) (50 mg) in a mixture of water (2 ml) and N,N-dimethyl-N-allylamine buffer (pH 9.5; 2ml). The resulting mixture was heated under nitrogen at 53° C. for 3 hours, when a ninhydrin test was negative. The cooled mixture was filtered and the filtrate concentrated to give a brownish solid residue. The solid residue was redissolved in water and passed through a column of Amberlite IR 120(Na) and then concentrated. The crude product was purified by gel filtration (Sephadex LH20; water) and freeze dried to give sodium 3,6-disulfonaphthylthiourea terminated poly-L-lysine BRI6047 as a white fluffy solid (87 mg).

EXAMPLE 3
Preparation of poly-L-lysyl [(8-octanamido)-5-acetamido-3,5-dideoxy-2-thio-D-glycero-α-D-galacto-2-nonulopyranosidoic acid]$_n$ BRI 6150

Poly-L-Lysine-NHCO [CH$_2$]$_7$—X

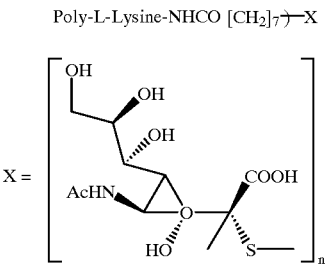

Methyl [(8-octanoic acid N-hydroxysuccinimide ester) 5-acetamido-4,7,8,9-tetra-O-acetyl-3,5dideoxy-2-thio-D-glycero-α-D-galacto-2-nonulopyranpsid]onate was prepared by the following procedure. To a solution of methyl 5-acetamido-4,7,8,9-tetra-O-acetyl-2-S-acetyl-3,5-dideoxy-2-thio-D-glycero-α-D-galacto-2-nonutopyranosonate (A. Hasegawa, J. Nakamura, and M. Kiso J. Carbohydrate Chemistry, 5(1), 11–19 1986) (100 mg.) in dry dimethylformamide (1 ml.) was added 8-bromooctanoic acid (41 mg.) and diethylamnine (280 mg.) and the solution stirred at 20° C. for 17 hours. Solvent was removed under vacuum and the residue partitioned between ethyl acetate and ice cold 5% hydrochloric acid. The organic layer was washed with water, dried, over sodium sulphate, and evaporated to give a residue (130 mg.). This was dissolved in ethyl acetate (5 ml.) and N-hydroxysuccinimide (26 mg.) and dicyclohexylcarbodiimide (46 mg.) were added. The mixture was stirred at 20° C. for 17 hours then the white precipitate was filtered off. The filtrate was concentrated and purified by flash chromatography on silica gel eluting with ethyl acetate. Fractions containing product were combined and evaporated to give a white foam 97 mg. 71%

To a solution of poly-L-lysine.HBr MW 150–300 Kd (22 mg.) in dry dimethyl sulphoxide (1 ml.) were added di-isopropylethylamine (15 mg.) and methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate (90 mg. ). The mixture was stirred under argon at 20° C. for 60 hours then solvent was removed under vacuum. The residue was dissolved in a freshly prepared 0.5M solution of sodium methoxide in methanol (4 ml.) and the mixture stirred for 48 hours under argon at 20° C. The solvent was evaporated and the residue dissolved in water (1.5 ml.) and stirred for 24 hours . This solution was s ubjected to size exclusion chromatography on Sephadex LH20 eluting with water. After lyophilisation, the product, poly-L-lysyl [(8-octanamido)-5-acetamido-3,5-dideoxy-2-thio-D-glycero-α-D-galacto-2-nonulopyranosidoic acid]$_n$ was obtained as a white powder 49 mg. 94%.

EXAMPLE 4
Preparation of Sodium 3,5-Dicarboxyphenylthiourea Terminated Polylysines A solution of poly-L-lysine.hydrobromide (4–15 K0 (Sigma Chemical Company) (50 mg) in water (2 ml) was added to a solution of sodium 3,5-dicarboxyphenyl isothiocyanate (305 mg) in water (3 ml) and the pH of the resulting solution adjusted to 9 with aqueous sodium bicarbonate. The solution was then heated at 53° C. under nitrogen for 4 hours. The solution was cooled and filtered, and the filtrate concentrated to give an off-white solid residue. The crude product was purified by gel filtration (Sephadex LH20; water) and freeze dried to give sodium 3,5-dicarboxyphenylthiourea terminated poly-L-lysine as a white fluffy solid (71 mg).

EXAMPLE 5
Preparation of Sodium 4-(Phosphonomethyl)phenylthiourea Terminated Polylysines Solid 4-(phosphonomethyl)phenyl isothiocyanate (231 mg; 1.0 mmol) was added to a solution of poly-L-lysine.hydrobromide (30–70 K) (Sigma Chemical Company) (50 mg) in a 1:1 mixture of pyridine/water. The pH of the mixture was adjusted to 9.5 with 1M sodium carbonate and the solution heated overnight at 53° C. under nitrogen. The mixture was cooled and filtered, and the filtrate concentrated to give a brown solid residue. The crude product was purified by gel filtration (Sephadex LH20; water) to give a brown solid (82 mg).

EXAMPLE 6
Preparation of 1-phosphono-oxyphenyl-4-thiourea Terminated Poly-L-lysine To a solution of poly-L-lysine hydrobromide (50 mg., Sigma P2636, 30–70 kilodaltons) in water (10 ml), heated and stirred at 53° C., was added 4-phosphono-oxyphenyl isothiocyanate (153 mg) and the pH of the mixture adjusted to 9.5–10 with 1M sodium carbonate solution. The mixture was heated and stirred at 53° C. for 5 hours and then filtered. The clear solution was purified by gel filtration on Sephadex LH20 eluting with water. The eluent was lyophilised to give the product as a white foam. 77 mg. 94%.

EXAMPLE 7
Preparation of benzamido-4-boronic Acid Terminated Poly-L-lysine

To a solution of poly-L-lysine hydrobromide (50 mg., Sigma P2636, 30–70 kilodaltons) in DMSO (10 ml), under an inert atmosphere, was added 4-carboxyphenylboronic acid N-hydroxysuccinimide ester (90 mg) and 1M sodium carbonate solution (2 ml) and the mixture stirred at 20° C. for 60 hours. Solvent was removed in vacuo and the residue dissolved in water (5 ml) and filtered. The clear solution was purified by gel filtration on Sephadex LH20 eluting with water. The eluent was lyophilised to give the product as a white foam. 50 mg. 90%.

EXAMPLE 8
Test for Antiviral Activity

The results of tests of activity of polyionic linear polymers of this invention against HIV 1, human and murine CMV, HSV 1 and 2 and human influenza A are shown in Tables 1 to 4, respectively. Table 5 shows the antiviral activity of the compound of Example 1 against a broad range of viruses. Tables 6 and 7 show the antiviral activity of the compounds of Examples 2 and 3, respectively, against RSV, MV CMV and influenza virus.

Using standard test protocols, antiviral activity was measured as an effective dose ($EC_{50}$) of the test compound that protects at least 50% of the cells used in the test from the effects of the virus. In addition, because of the requirement for safety to the cells by the test compound, cell cytotoxicity ($CC_{50}$) is determined as the concentration of the test compound that kills 50% of uninfected cells. The total antiviral activity can be expressed as the selectivity index (SI), $CC_{50}/EC_{50}$.

TABLE 1

Activity of BRI Linear Polymers against HIV

| Compound | Virus Strain | Conc. | $EC_{50}$ | $CC_{50}$ | Antiviral Index-SI | Structure |
|---|---|---|---|---|---|---|
| BRI 6047 | HIV 1 IIIB | µM | 0.002 | >3.44 | >1720 | Poly-l-Lysine(15–30K) Naphthyl di $SO_3Na$ |
| BRI 2967 | HIV 1 IIIB | µM | 0.014 | >20.8 | >1480 | Poly-l-Lysine(4–15K) Phenyl-$SO_3Na$ |
| BRI 2994 | HIV 1 IIIB | µM | 0.60 | >62.5 | >1040 | Poly-l-Lysine(1–4K) Phenyl-$SO_3Na$ |
| BRI 2995 | HIV 1 IIIB | µM | 0.005 | >5.7 | >1140 | Poly-l-Lysine(15–30K) Phenyl-$SO_3Na$ |
| BRI 2996 | HIV 1 IIIB | µM | 0.007 | >0.8 | >114 | Poly-d-Lysine(150–300K) Phenyl-$SO_3Na$ |
| Standards | | | | | | |
| AZT | HIV 1 IIIB | µg/ml | 0.0001 | 1.17 | 15,775 | |
| DS5000 Dextran Sulfate | HIV 1 IIIB | µg/ml | 0.0263 | >250 | >9,497 | |

TABLE 2

Activity Against Cytomegalovirus (Davis strain) in Cell cultures.

| Compound | $EC_{50}$ µg/ml | $CC_{50}$ µg/ml | Ganciclovir $CC_{50}$ µg/ml | Cells used |
|---|---|---|---|---|
| BRI 2995 | | | | |
| HCMV CPE Inhibition | 2.7 | >100 | 0.1 | HFF |
| HCMV Plaque Reduction | 9.1 | >100 | 0.2 | HFF |
| MCMV Plaque Reduction | 17.7 | 100 | 0.5 | MEF |

HCMV = Human CytoMegalo Virus; MCMV = Murine (Mouse) CytoMegalo Virus.
Tests in Human Embryonic Lung cells (HEL); Human Foreskin Fibroblasts (HFF); Mouse Embryonic Fibroblasts (MEF).
$EC_{50}$ CPE = Inhibitory concentration to reduce virus CytoPathic Effect on cells by 50%.
$CC_{50}$ = Cytotoxic concentration required to reduce HEL cell growth by 50%.

TABLE 3

Activity Against Herpes Simplex 1 & 2 in Cell cultures.

| BRI 2995 | $EC_{50}$ µg/ml | $CC_{50}$ µg/ml | Ganciclovir $CC_{50}$ µg/ml | |
|---|---|---|---|---|
| HSV-1 CPE Inhibition | 0.88 | >100 | 0.06 | HFF |
| HSV-1 Plaque Reduction | 25.9 | >100 | 0.3 | HFF |
| HSV-2 CPE Inhibition | 1.4 | >100 | 0.2 | HFF |
| HSV-2 Plaque Reduction | 13.6 | >100 | 0.6 | HFF |

HSV-1 = Human Herpes Simplex Virus-1 (Mucosal Herpes).
HSV-2 = Human Herpes Simplex Virus-2 (Genital Herpes).
Tests in Human Foreskin Fibroblasts (HFF).
$EC_{50}$ CPE = Inhibitory concentration to reduce virus CytoPathic Effect on cells by 50%.
$EC_{50}$ Plaque Reduction = Inhibitory Concentration to reduce virus plaque by 50%.
$CC_{50}$ = Cytotoxic concentration required to reduce cell growth by 50%.

TABLE 4

BRI 6150
Poly-L-Lysine (590K Average (NHCO $[CH_2]_7$—)—X $X=$ 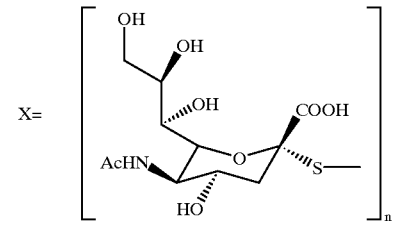

Activity Against Two Strains of Influenza A virus

| Compound | $EC_{50}$ µg/ml Tokyo Strain | $EC_{50}$ µg/ml G70C Strain |
|---|---|---|
| BRI 6150 | 0.03 | 0.04 |

TABLE 5

Poly-L-Lysine (NHCSNHPhSO$_3$Na)x 26-K-53K

| BRI 2995 ARB 95-336 | CPE-inhibition $EC_{50}$ ($CC_{50}$) µg/ml | Viral count or Plaque Reduction $EC_{50}$ ($CC_{50}$) µg/ml | | CPE-inhibition $EC_{50}$ ($CC_{50}$) µg/ml SI | Viral Count $EC_{50}$ ($CC_{50}$) µg/ml SI | |
|---|---|---|---|---|---|---|
| Virus Strain | | | | | | Ribavirin |
| RSV; Long | 10 (>1000) | >100 | 10 (100) | 10 (560) | 10 (200) | 56 | 200 | 1 |
| | 0.3 (30) | 100 | >0.1 (30) | >300 | 7 (90) | 13 | 1 (40) | 40 |
| RSV; A2 | 0.5 (55) | 110 | 0.1 (>100) | >1000 | 13 (400) | 31 | 2 (>1000) | >500 |
| | | | | | | | Ganciclovir | |
| CMV; Davis | 2.7 (>100) | >37 | 9.1 (>100) | >11 | 0.1 | | 0.2 | |
| MCMV | | | 17.7 (>100) | >5.7 | 0.6 | | | |
| | | | | | | | Acyclovir | |
| VZV | | | 93.3 (>100) | >1.1 | | | 0.5 | |

TABLE 5-continued

Poly-L-Lysine (NHCSNHPhSO$_3$Na)x 26-K-53K

| BRI 2995 ARB 95-336 | CPE-inhibition EC$_{50}$ (CC$_{50}$) μg/ml | | Viral count or Plaque Reduction EC$_{50}$ (CC$_{50}$) μg/ml | | CPE-inhibition EC$_{50}$ (CC$_{50}$) μg/ml SI | | Viral Count EC$_{50}$ (CC$_{50}$) μg/ml SI | |
|---|---|---|---|---|---|---|---|---|
| HSV-1 | 0.88 (>100) | >125 | >100 (>100) | 0 | 0.06 | | 0.3 | |
| HSV-2 | 1.4 (>100) | >71 | >100 (>100) | 0 | 0.2 | | 0.6 | |
| | | | | | | | Control drug (?) | |
| Flu A; H$_1$N$_1$ | 2.0 (538) | 269 | 2.4 (261) | 109 | 6.1 (>100) | >16 | 5.6 (>100) | >18 |
| Flu B | 6.5 (501) | 77 | 6.5 (171) | 28 | 3.3 (100) | >30 | 6.2 (>100) | >16 |
| | Concentrations μM | | | | | | Zidovudine | |
| HIV-1; IIIB | 0.15 (>250) | >1,680 | (4.38) | 11,840 | 0.00037 | | | |
| HIV-2; ROD | 2.32 (>250) | >108 | | | | | | |

Viruses:
RSV = Respiratory Syncytial Virus;
HSV Herpes Simplex Virus (type 1 = mucosal; type 2 = genital)
CMV = Cytomegalovirus;
VZV = Varicella Zoster Virus;
MCMV = Murine Cytomegalovirus
Flu A = Influenza A Virus;
Flu B = Influenza B Virus;
HIV-1 & 2 = Human Immunodeficiency Virus type 1 and 2.
Terms:
CPE = Cytopathic effect of virus on infected cells or when measure of cell toxicity (CC$_{50}$) the effect of compound alone on the cell.

TABLE 6

Poly-L-lysine CONH.CH$_2$CH$_2$NHCSNH[Naphth-3,6-(SO$_3$Na)$_2$] (37K-75K)

| BRI 6047 ARB-96-222 | CPE-inhibition EC$_{50}$(CC$_{50}$) μg/ml SI | | PR = Plaque Reduction NR = Neutral Red cell count EC$_{50}$(CC$_{50}$) μg/ml SI | | CPE-inhibition EC$_{50}$(CC$_{50}$) μg/ml SI | | PR = Plaque Reduction NR = Neutral Red cell count EC$_{50}$(CC$_{50}$) μg/ml Sl | |
|---|---|---|---|---|---|---|---|---|
| Virus; Strain | | | | | Control Drugs Ribavirin | | | |
| RSV; A2 | 1 (110) | 110 | NR <1.0 (100) | >100 | 7(90) | 13 | NR 1.0 (40) | 40 |
| RSV; A2 | Virus Yield EC$_{50}$ (CC$_{50}$) | | EC$_{90}$ μM SI = CC$_{50}$/EC$_{90}$ | | Virus Yield EC$_{50}$CC50 | | EC90 SI=CC$_{50}$/EC$_{90}$ | |
| RSV; A2 | 1.0 (34) | | 3.0 | 11 | 6.0 (71) | | 6.0 | 12 |
| CMV | 18 (55) | 3 | | | 25(118) | | 5 | |
| | | | | | | | Control Drug (2) | |
| Flu A; H1N1 | <1.0(599) | >599 | NR <1.0(178) | >178 | 5.6 (>100) | >18 | 5.0 (>100) | >20 |
| Flu A; H1N1 | 15 (>100) | >6.7 | NR 14(>100) | 7.6 7.1 | >16 (>100) | | NR 5.0 (>100) | >13 |
| Flu A; H1N1 | 3.8 (>100) | 26 | NR 12 (>100) | 5.0 >8.3 | >20 (>100) | | NR 5.4 (>100) | >18 |
| Flu A; H1N1 | 3.2 (>100) | >57 | NR 7.2 (>100) | 2.2 >14 | >45 (>100) | | NR 2.8 (>100) | >36 |
| Flu A; H1N1 | Virus Yield EC$_{50}$(CC$_{50}$) 0.53 (140) | | EC$_{90}$ SI = CC$_{50}$EC$_{90}$ 0.8 | 175 | Virus Yield EC$_{50}$CC$_{50}$ 4.7 | (24) | EC$_{90}$ SI = CC$_{50\ EC90}$ 3.0 | 8 |
| Flu B | 13 (487) | 37 | NR 19 (267) | 14 | 4.3 (100) | >23 | 5.5 (>100) | >18 |
| Flu B | Virus Yield EC$_{50}$ (CC$_{50}$) 2.2 (140) | | EC$_{90}$ SI = CC$_{50}$/EC$_{90}$ 49 | 2.8 | Virus Yield EC$_{50}$CC$_{50}$ 1.7 | (24) | EC$_{90}$ SI = CC$_{50}$EC$_{90}$ 1.5 | 16 |

TABLE 7

| | Poly-L-lysine-{NH.CO.(CH₂)₇S-[2-5-acetyl-neuraminic acid]}ₓ (590k) | | | |
|---|---|---|---|---|
| BRI 6150 AR8-96-227 | CPE-inhibition EC₅₀ (CC₅₀) μg/ml SI | CPE-inhibition EC₅₀ (CC₅₀) μg/ml SI | CPE-inhibition EC₅₀ (CC₅₀) μg/ml SI | CPE-inhibition EC₅₀ (CC₅₀) μg/ml SI |
| Virus; Strain Ribavirin | | | | Control Drug |
| RSV; A2 | | <1.0 (>1000) >1000 | 13.0 (400) 31 | |
| RSV; A2 | | <1.0 (>1000) >1000 | | 2.0 >500 |
| Flu B | <1 (>720) >720 | NR | NR | (>1000) |
| | | <1 >1000 >1000 | 1.8 >56 (>100) | |
| RSV, A2 EC₅₀ (CC₅₀) | Viral Yield SI = CC₅₀/EC₉₀ 3.0 (>1000) | EC₉₀ EC₅₀ (CC₅₀) 2.0 >500 | Viral Yield SI =CC₅₀EC₉₀ 6.0 (71) | EC₉₀ 6.0 12 |

What is claimed is:

1. An antiviral compound comprising a linear, non-carbohydrate polymer having a plurality of side chain groups, wherein at least one of said side chain groups has an anionic-containing moiety bonded or linked thereto, wherein said anionic-containing moiety is selected from the group consisting of:
   (i) neuraminic acid-containing moieties which are modified by substitution in the 4-position thereof; and
   (ii) sialic acid-containing moieties which are modified by substitution in the 4-position thereof.

2. An antiviral compound according to claim 1, comprising a linear polymer of the formula:

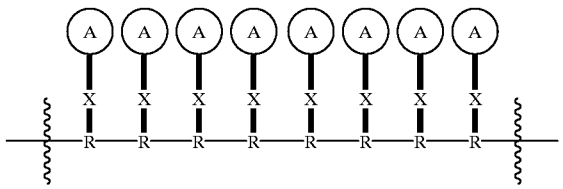

I wherein:
   R is a non-carbohydrate monomer unit forming a linear polymer backbone;
   X is an optional linking group on the side chain groups of monomer units R; and
   A is an anionic-containing moiety as defined in claim 1.

3. The antiviral compound according to claim 2, wherein said linear polymer has a median range of molecular weight distribution from 1,000 to 1,000,000.

4. The antiviral compound according to claim 3, wherein said median range of molecular weight distribution is from 10,000 to 600,000.

5. The antiviral compound according to claim 2, wherein said monomer unit R is an amine moiety or an amide moiety.

6. The antiviral compound according to claim 5, wherein said monomer unit R is an amino acid.

7. The antiviral compound according to claim 6, wherein said amino acid is lysine.

8. The antiviral compound according to claim 2, wherein said linking group X is a functional linking group selected from the group consisting of an ester, an amide, an ether, a thioether, an amine, an urea, a thiourea, a carbamate and a carbonate.

9. The antiviral compound according to claim 2, wherein said linking group X is a spacer group selected from the group consisting of an alkyl chain, a branched alkyl chain, an alkoxy chain, a polyalkoxy chain, an alkylthio chain, a polyalkylthio chain, an alkenyl chain, a multiple alkenyl chain, an alkynyl chain, and a multiple alkynyl chain.

10. The antiviral compound according to claim 9, wherein said linking group X is a substituted chain.

11. The antiviral compound according to claim 2, wherein said linking group X is a group of the formula:

—(CH₂)n-Z—(CH₂)n-;

wherein Z is selected from the group consisting of —CH₂—, —CH═CH—, —C≡C—, —O— and —S—, and wherein n is an integer of from 1 to 15.

12. The antiviral compound of claim 1, wherein said anionic-containing moiety is bonded by an amide or a thiourea linkage to a reactive functional side chain group of said linear polymer.

13. The antiviral compound of claim 12, wherein said reactive functional side chain group is selected from the group consisting of an amine group, a sulfonyl group, and a hydroxy group.

14. The antiviral compound according to claim 1, wherein the substituent in the 4-position of said neuraminic acid-containing moieties or said sialic acid-containing moieties is selected from the group consisting of amino, cyano, azido and guanidino groups.

15. A pharmaceutical composition for preventing or treating a viral infection of an animal comprising a compound of claim 1 and a pharmaceutically acceptable carrier or diluent.

16. A method for preventing or treating a viral infection of an animal comprising administering to said animal an amount of the compound of claim 1 sufficient to prevent or treat said viral infection.

17. The method according to claim 16, wherein said viral infection is caused by a virus selected from the group consisting of HIV-1, HIV-2, hepatitis B virus, hepatitis C virus, bovine viral diarrhoea virus, Japanese encephalitis virus (JEV), human influenza virus A, human influenza virus B, rhinovirus, corona virus, human parainfluenza virus, respiratory syncytial virus (RSV), varicella zoster virus VZV, human cytomegalovirus (CMV), Epstein Barr virus (EBV), human papilloma virus (HPV), adenovirus, herpes simplex virus (HSV) type 1, herpes simplex virus (HSV) type 2, measles virus, and vesicular stomatitis virus (VSV).

18. A process for making a composition useful in preventing or treating a viral infection comprising combining the compound of claim 1 with pharmaceutically acceptable carrier or diluent.

* * * * *